United States Patent [19]

Hughes et al.

[11] Patent Number: 4,544,516

[45] Date of Patent: Oct. 1, 1985

[54] COLLAGEN ORIENTATION

[75] Inventors: Kenneth E. Hughes, Gahanna; Timothy B. Hutson, Columbus; David J. Fink, Marble Cliff, all of Ohio

[73] Assignee: Battelle Development Corporation, Columbus, Ohio

[21] Appl. No.: 509,423

[22] Filed: Jun. 30, 1983

Related U.S. Application Data

[63] Continuation-in-part of Ser. No. 402,722, Jul. 28, 1982, abandoned.

[51] Int. Cl.$^4$ ............................ B29D 7/02; D01D 1/02
[52] U.S. Cl. .................................... 264/108; 260/123.7; 264/202
[58] Field of Search ....................... 264/108, 164, 202; 260/123.7

[56] References Cited

U.S. PATENT DOCUMENTS

| | | | |
|---|---|---|---|
| 2,425,550 | 8/1947 | Lundgren | 264/164 |
| 2,598,608 | 5/1952 | Salo et al. | 260/123.7 |
| 2,838,363 | 6/1958 | Veis et al. | 264/164 |
| 2,935,413 | 5/1960 | Veis et al. | 106/124 |
| 3,284,557 | 11/1966 | Polansky | 264/238 |
| 3,433,864 | 3/1969 | Highberger et al. | 260/123.7 |
| 4,242,291 | 12/1980 | Hughes et al. | 260/123.7 |
| 4,416,814 | 11/1983 | Battista | 260/123.7 |

FOREIGN PATENT DOCUMENTS 1198310  7/1970  United Kingdom ................ 530/356

*Primary Examiner*—James Lowe
*Attorney, Agent, or Firm*—Barry S. Bissell

[57] ABSTRACT

Monomeric collagen is oriented in solution and the orientation is retained in the resulting gel by setting up convective flow paths in the solution during gelation. The convection is induced by uniform peripheral heating of the cold, collagen solution in a small-diameter cylinder. Oriented collagen produced in this manner has excellent wet strength for use in implants for natural reconstruction of body collagen.

16 Claims, No Drawings

COLLAGEN ORIENTATION

This application is a continuation-in-part of our earlier filed application Ser. No. 402,722, filed July 28, 1982 and now abandoned.

TECHNICAL FIELD

For over 20 years, collagen has been investigated as a biomaterial for use in a great variety of therapeutic and prosthetic applications. For many of these applications, finely divided or micronized collagen suspensions have been prepared by mechanically reducing the size of collagen-containing solids, such as those derived from animal skin. These suspensions could then be fabricated into sheets (membranes) or other structures by concentrating the suspension (e.g., by filtration), then drying to form a solid matrix. Collagen materials are rather easy to fabricate by such processes, additives are readily incorporated, and stabilization by chemical or ultraviolet cross-linking is possible. However, in applications where unique structural properties are required, for example in prosthetic devices to replace the lamellar matrix existing in the cornea of the eye or the highly ordered parallel structure of the tendon, the properties of micronized collagen preparations are inadequate.

A second, known method for producing collagen structures (which is improved by this invention) comprises reconstituting monomeric collagen. When a solution of monomeric collagen at neutral pH and moderate ionic strength is heated, a spontaneous self-assembly process is initiated, which leads to the production of native-type collagen fibers. The specific mechanism involved in this in vitro polymerization process (also referred to herein as gelation or fibrillogenesis), is not well understood, but appears to involve two clearly distinguishable phases. First, a "lag" phase occurs during which neither the solution turbidity nor viscosity changes appreciably. Then, a "growth" phase follows, characterized by an increased solution turbidity and formation of distinct fibril structures. These fibrils eventually grow into a porous gel structure in which most of the collagen is present in a highly ordered, insoluble fibrillar matrix.

Gelation, or polymerization, of certain collagens in solution may also be induced by changes in pH. An example of preparation of monomeric collagen solutions and inducement of gelation by a combination of pH and temperature change, followed by the orientation of the gelled collagen, is shown in U.S. Pat. Nos. 2,838,363 and 2,935,413.

SUMMARY OF THE INVENTION

It is an object of the present invention to provide useful, high-strength biomaterials made of native-type collagen matrices.

It is also an object to produce the native-type collagen by thermally induced fibrillogenesis from monomeric solutions.

It is further an object to provide a method for uniformly orienting the monomeric collagen molecules in the solutions and maintaining such orientation in the collagen fibrils of the gelled material.

In accordance with the objectives, the invention is a method of producing a collagen material having an oriented fibril structure. The material is produced by the method of introducing a substantially laminar flow in a predominantly monomeric collagen solution and thermally inducing fibrillogenesis thereof. A small diameter tube is preferably used to induce convective flow on the solution. The tube should have a cross section of less than about 120 square millimeters and is preferably square or circular. A particularly preferred method comprises thermally gelling a 0.6–3.0 mg/ml collagen solution in a circular, cylindrical tube of less than 12 millimeters in diameter at a temperature of between about 20° C. and 40° C. Vertical positioning of the tube longitudinal axis during gelation results in better collagen fibril orientation in the gel than horizontal positioning of the axis.

Laminar flow may also be introduced by a low-flow rate extrusion of the monomer solution through a heated tube. Dwell time is adjusted so that heating and fibrillogenesis take place in approximately the time required for the solution to traverse the tube.

DESCRIPTION OF THE INVENTION

Collagen, a natural biopolymer and protein, makes up about 35 percent of the protein in body tissues and forms the primary structure of tendons, skin, bones, and blood vessels. Most of the body's organs and tissues are supported by this fibrous substance, which is found interwoven throughout both hard and soft tissues, often in combination with other materials.

Soluble collagen derived from animal tissues can be reconstituted in suspension to form a fibrous gel-like substance, which can subsequently be processed for use as a biomaterial. In vitro, the polymerization of monomeric collagen is termed "fibrillogenesis". The resultant material has potential uses in producing biomedical products such as artificial corneas, vascular grafts, tendon grafts, and many other prosthetics.

Current slurry-cast or extruded (randomly oriented), collagen materials are too weak and degradeable for most such uses. Synthetic supports made of silicones or resin materials are therefore used to augment the implant, but they remain as permanent invaders of the body.

Collagen molecules exist in the unaggregated state as rod-like structures, approximately 3000 Å long and 15 Å in diameter, composed of three peptide chains intertwined in a triple helix formation. Consistent orientation of such molecules in the aggregated state is expected to result in improved strength and other properties, at least in the axial direction. Some attempts have been made to orient the collagen fibrils, but these attempts have typically comprised physical force applied to the gelled or partially gelled material, eg. by mechanical stretching or extrusion. On the contrary, the present invention is a method for orienting the unaggregated collagen molecules by inducing flow in the monomer solution during the thermally induced fibrillogenesis process. The orientation is maintained in the aggregated collagen gel, resulting in high strengths in materials processed from these gels.

Flow may be introduced in the monomer solution by any known means. Active means such as an impeller, a rotating container or a positive displacement pump may be used, for example. In the present invention, the means for orienting the collagen molecules may also comprise the means for inducing the fibrillogenesis. In the preferred method, heat is applied to an elongated, small-diameter, heat-conducting tube containing a predominantly monomeric collagen solution. Fluid motion is induced in the solution by natural convection as the tube is heated externally by an appropriate heat-transfer medium. For example, if cold collagen solution is placed in a small-diameter, quartz tube and heat is supplied radially by immersing the tube in a warm gaseous or liquid medium, convective fluid motion is superimposed on the fibrillogenesis process. When the tube axis is vertically aligned, convection "cells" are established in which fluid motion occurs predominantly in the axial direction.

The collagen molecules are rotated by the solution flow, resulting in the orientation of the molecules with their axes parallel to the direction of fluid flow (eg. more or less along the tube axis in the preferred, small, inclined tubes). In this position, fluid drag on the particles is minimized. As polymerization of monomers proceeds, the larger aggregates have an even larger aspect ratio and will, therefore, display an even greater tendency to be oriented in the solution flow. At some point in the fibrillogenesis process, very large fibrils are produced, which are immobilized in the growing collagen gel matrix. This is the inventive method that has been observed to cause the residual orientation of formed fibrils. We term it the "flow orientation" process. Though useful with a variety of flow methods, we will describe the orientation method more particular with respect to convective flow in small tubes.

EXTRACTION AND PREPARATION OF MONOMERIC COLLAGEN

The monomeric collagen solutions are conventional in the art. Collagen material may be obtained from commercial suppliers. Alternatively, the collagen material may be produced in the laboratory in a manner similar to the following:

(1) isolate collagen-containing tissue,
(2) wash with buffer,
(3) segment tissue, e.g. by freeze-fracturing,
(4) solubilize and extract desired collagen fraction in buffered salt solution, enzyme solution (e.g., pepsin or Pronase ®) or organic acid solution (e.g. acetic, citric, etc.),
(5) purify collagen by a series of salt precipitations,
(6) store frozen in acid solution until needed. We refer to solutions in this transitory state as stock solutions.

Material purchased from suppliers is generally in this state when delivered. When ready to use, these additional steps are performed on either in-house or purchased stock solutions:

(7) dialyze at 4° C. to desired pH,
(8) remove collagen aggregates by gel/melt cycles, then centrifuge cold to remove irreversible aggregates,
(9) bring to desired concentration, and
(10) introduce into gelation container and elevate temperature to gel.

Known collagen additives, such as elastin and GAG (glycosaminoglycan) may be added to the solution before gelling or may be perfused through the gel prior to cross linking.

FIBRILLOGENESIS

As noted above, stock solution is adjusted to desired concentration using dialysis buffer at the desired ionic strength and pH. The resultant solution is then centrifuged to remove residual aggregates. The concentration range is not critical, and is somewhat dependent on the type of collagen used. Solutions of 0.6–1.5 mg/ml have been found to give the most desirable orientation with lathyritic collagen produced by salt extraction in the lab. Purchased material, extracted by an enzyme process, requires concentrations of about 2.0–3.0 mg/ml to give similarly desirable results. This may be due to the absence of the telopeptide end regions on these collagen molecules. Solutions of less than about 0.3 mg lathyritic collagen per milliliter (0.6 mg/ml enzyme-treated collagen) produces gels of poor stability. The reduction of fibril interaction in the lower concentration gels also tends to somewhat limit orientation.

Solution pH has an effect on gel time, but is substantially non-critical to fibril orientation. The range of about pH 6–8 is preferred.

The temperature during fibrillogenesis has been found to affect orientation to a limited degree. In performing the gelation, the collagen solution is placed in the hereafter-described tube at less than about 4° C. Heat is then applied to the outer periphery of the tube, preferably uniformly, to raise the temperature of the solution to the desired level. A water or air jacket around the tube is particularly desirable. Heating induces the fibrillogenesis, and with the proper tube dimensions, also induces the convective flow in the solution. Of course, convection also tends to distribute the heat rapidly throughout the solution so that the solution appears to gel uniformly throughout the tube.

Gelation temperatures in the range of 20° C. to 40° C. generally produce the preferred orientation. Using tubes about 6 mm in internal diameter, a time of about 1–6 minutes was required to raise the temperature of the solution to within 5% of the equilibrated temperature of the jacket. Temperatures of less than 25° C. can be used but result in very slow gelation. Temperatures above about 35° C. appear to result in less aggregation (more disperse, small aggregates) than produced with temperatures below about 35° C. However, good orientation and mechanical properties appear to be introduced up to a maximum temperature of about 40° C.

Whatever temperature within the preferred range is used, the heating of collagen solution in an elongated, small-diameter tube results in fluid motion in convection cells therein. In vertically aligned tubes having a height of at least 4 times the thickness, we have found that these convection cells are substantially ellipical in shape with the major axis parallel to the tube axis. We believe that in vertically disposed tubes, gravitational and other forces tend to elongate the convection cells along the tube axis and subsequently result in better fibril orientation than in tubes with less inclination. We believe that the greater the inclination toward the vertical, the more elongated the convective cells are, and the more consistent the longitudinal alignment. In the horizontal tubes, the longitudinal orientation is consistent in the smaller (2 and 4 mm) tubes, but not as consistent as in the vertically gelled material. In larger tubes, the horizontally gelled material has orientated fibrils and improved strength over cast films, but the orientation is not particularly consistent in the longitudinal direction, probably owing to less eliptical convective flow cells. The fibril orientation in the gels from the horizontally gelled, larger diameter tubes is more like that in the cast films than in the vertically gelled material.

The tubes are preferably elongated and have widths and thicknesses (of the cross section) which are substantially similar, if not equal. For example, the width is preferably less than two times the thickness, whereas the heighth is preferably at least four times the thickness. Square or circular cross sections are preferred.

The simple cross section and high aspect ratio have been observed to result in elongated convection cells within the tubes which improve fibril orientation in the resulting collagen gels. Rectangular cross sections may contribute toward multiple side-byside convection cells which are not as elongated and may not consistently orient the collagen along the tube longitudinal axis as well as square or circular cross sections.

Tubes which have cross sections exceeding about 120 square millimeters in area appear not to provide as good fibril orientation as smaller tubes. The reason for this is unknown, but probably results from the less-elongated shape of convection cells which are induced by uniform, external heating of the tubes. In experiments comparing the properties of collagen gels from circular tubes of different diameters, optical and mechanical measurements showed that the convective orientation effect (improvement over horizontal samples) was maximized in 8 mm ID vertically aligned tubes. Lesser improvements occurred in tubes of smaller or larger diameter but even at 12 mm ID, the samples were oriented and exceeded the strength of slurry cast (unoriented) samples and horizontally gelled tube samples.

REMOVAL AND MATERIAL TREATMENT

After gelation, collagen gels may be removed by first cross-linking the material and then physically removing the gel from the containers. The gel may be cross-linked by ultraviolet light, but this can result in localized heating and denaturation of the collagen. Chemical cross-linking by perfusion of a suitable agent through the semi-permeable gel is therefore preferred, for example with a glutaraldehyde solution. Cross linking may be done after drying and rehydrating of the gel but is preferably done before, in order to strengthen the gel. The gel could also be cross linked and dried at the same time by heating to an appropriate temperature.

Collagen gels which are oriented by flow orientation according to the invention contain substantially above 90 w/o water. In order to form biomaterial implants therefrom the gels must be dried below the point of irreversible shrinkage. This may occur (depending on the type of collagen and other processing variables) at below about 20 w/o water, but usually at below about 10 w/o water. Above this point of irreversible shrinkage, the "dried" ribbon may be rehydrated to a gel of nearly the original size (and strength). Below this point, the dried ribbon expands only slightly and retains substantial strength upon rehydration.

Biomaterial implants, such as tendon and vascular grafts, are then fashioned from the dried collagen ribbon by rehydration thereof and by layering, weaving or twisting, etc. the rehydrated ribbons into the desired shape and bonding them together.

DESCRIPTION OF THE PREFERRED EMBODIMENTS

Example 1-Horizontal and Vertical Convective Orientation

Collagen stock solutions were prepared as follows:
(1) wash excised lathyritic rat skins in a Tris buffered solution containing EDTA and a proteolytic enzyme inhibitor, e.g. phenyl methyl sulphenyl fluoride;
(2) freeze skins and fracture into small pieces;
(3) extract washed tissue three times with three volumes of 0.10M NaCl in Tris buffer (50 mM, pH 7.4);
(4) extract the residual tissue three times with three volumes of 0.95M NaCl in Tris buffer (pH 7.4, 50 mM);
(5) centrifuge (18,000×g for 1 hr) extraction solutions from step 4 and combine the supernatants;
(6) to the pooled supernatants from step 5, add NaCl to a final concentration of 17 percent. Collect precipitates by centrifugation at 18,000×g for 1 hr. Decant and discard supernatants. Redissolve the precipitates in the original extraction buffer and repeat precipitation and resoluablization for a total of three times.
(7) redissolve the final precipitates in 0.5M acetic acid and store frozen at −20° C. This material is referred to hereafter as the stock lathyritic collagen solution.

Neutral-pH collagen for fibrillogenesis was prepared by dialysis at 4° C. of an aliquot of the above stock solution (in 0.5M acetic acid) against 3 to 4 changes (4 liters each) of 32.7 mM $NaH_2PO_4$ at ionic strength=0.15 and the desired pH.

After dialysis, a further purification of the collagen was accomplished by gelling the solution at 30° C. for approximately 25–35 minutes. The resultant collagen gel was then centrifuged at room temperature and the supernatant poured off. The collagen pellet was brought back to 40 percent of the original volume with dialysis buffer and held at 4° C. to resolubilize. The solution was centrifuged to remove insoluble aggregates.

The collagen solutions, were then deaerated and loaded into open-ended, circular-cross-section, quartz gel tubes having inside diameters of 6 mm and lengths of 100 mm. At either end, special silicone rubber stoppers were inserted. Standard hypodermic needles were used for both filling and venting of the gel tubes. All the above operations were performed in a cold room at 4° C. and the loaded tubes were stored and transported in an ice bath.

The filled tubes were transferred singly from the ice bath to an air-heated chamber. The chamber was heated by circulating warm air through the system at a constant temperature. A baffle system surrounded the tube to ensure uniform heating. To examine the effect of sample position relative to the gravitational vector, the sample tube axes were positioned either vertically or horizontally during the process of thermal gelation. The resulting gels were analyzed for collagen matrix morphology, and (in their dried form) for mechanical strength and optical properties.

Table 1 summarizes the results of these experiments and compares various properties for lathyritic collagen prepared as described above, and Vitrogen 100 ®, an enzyme-treated collagen produced by Collagen Corp., Palo Alto, Calif. All gels were cross-linked with a 1% glutaraldehyde perfusion and removed from the tubes. Some samples were dehydrated by removing the cross-linked gel from the tube, and gradually air-drying on a non-wettable plastic substrate. The thin, insoluble strip made by this drying process is hereafter called a collagen ribbon, whether in a dry or rehydrated state.

Gel morphology was preserved in wet samples after removal from the gelation tubes by embedding cross-linked gels in an epoxy matrix. Sections of these samples, when observed by optical microscopy, exhibited pronounced fibril orientation parallel to the axis of the vertically positioned samples. Other samples, gelled horizontally, showed a more random structure but still revealed greater orientation, in many cases than flat cast samples. This difference in structure is also revealed by characterization of the optical properties of dehydrated samples, and is manifested in improved mechanical properties.

The rotation of plane-polarized light by the sample was used as an indicator of fibril orientation in the dried ribbon. Samples were placed on the indexed rotary stage of an optical microscope, between two polarizing filters aligned orthogonally (the extinction position). Transmitted light intensities were measured with each sample aligned at 45° ($I_{45}$) and parallel ($I_o$) to the first polarizing filter. The ratio of these intensities ($I_{45}/I_o$), defined hereafter as the Polarized Light Ratio (PLR), is directly related to the optical anisotropy of the sample. We have consistently observed that PLR's are greater for collagen gels that were vertically positioned than through similar gels that were horizontally positioned during fibrillogenesis.

TABLE 1

PROPERTIES OF COLLAGEN GELS AS AFFECTED BY SAMPLE ORIENTATION DURING GELATION*

|  | Lathyritic Collagen (1.5 mg/ml) | Vitrogen 100 ® (3.0 mg/ml) |
|---|---|---|
| Vertical Tube Axis |  |  |
| Median Yield Stress (g/mm$^2$) | 2000 | 2200 |
| Range (g/mm$^2$) | 1100–2500 | 1500–2800 |
| Median Polarized Light Ratio | 31.3 | 18.0 |
| Range | 24.2–41.7 | 6.5–22.0 |
| Horizontal Tube Axis |  |  |
| Median Yield Stress (g/mm$^2$) | 900 | 1700 |
| Range (g/mm$^2$) | 700–1200 | 1200–1900 |
| Median Polarized Light Ratio | 7.0 | 10.0 |
| Range | 1.2–15.0 | 6.0–11.0 |

*In 6 mm ID × 100 mm long quartz tubes at pH 7.0 and 30° C. Approximate cross-sectional area of ribbons: lathyritic collagen, 0.188 mm$^2$; Vitrogen 100 ®, 0.125 mm$^2$.

Prior to tensile testing, the ribbon material was rehydrated by immersion in normal saline solution for at least 4 hours. Upon rehydration, the material swelled to about 150% of its dry volume. Rehydrated collagen prepared by these methods exhibited elastic behavior under increasing tensile load, until either tearing or a total break occurred. The fibril orientation in gels formed vertically appeared to result in enhanced mechanical properties in the axial direction. Mechanical strength, determined by standard tensile testing methods, was greater in rehydrated collagen ribbons processed from these gels (see Table I).

EXAMPLE 2-Cast Film Morphology

Collagen solutions were cast to solution depths of 1, 3, and 6 mm, in small, water-jacketed beakers of about 25 mm inner diameter. Cold collagen solutions were pipetted directly into the beakers which were connected into a pre-heated, circulating water loop at 30° C. This controlled system is analogous to normal thermal gelation on glass plates or microscopic slides, as often used for scientific investigation of collagen fibril formation, and was intended to contrast the properties of random fibril matrices with the oriented fibril matrices made according to the invention. The properties of the dehydrated material made from these cast gels are shown in Table II.

The slightly improved Polarized Light Ratio and mechanical properties observed in the 3 and 6 mm gels are believed to be due to some convective flow orientation in these thicker films but not in a unidirectional manner across the sample. Random sectioning of these samples for microscopic inspection and tensile testing revealed no preferential alignment of the collagen in any direction. When compared with the dramatic improvement in fibril orientation documented in Example 1, these cast films demonstrate the properties of relatively isotropic matrices formed by the thermal gelation process.

TABLE II

PROPERTIES OF DEHYDRATED CAST FILMS

| Collagen Type | Gel Depth (mm) | Tensile Stress* (g/mm$^2$) | Polarized Light Ratio |
|---|---|---|---|
| Lathyritic | 1 | 330 | 1.0 |
| (1.5 mg/ml) | 6 | 330 | 1.8 |
| Vitrogen 100 ® | 1 | 700 | 1.0 |
| (3.0 mg/ml) | 3 | 1300 | 2.4 |
|  | 6 | 1900 | 2.5 |

*Tensile stress normalized by using a common shrinkage factor based on typical shrinkage of 6 mm diameter cylindrical gels.

Example 3-Effect of Tube Diameter on Orientation

To demonstrate the effect of container dimensions on the simultaneous polymerization and alignment of collagen fibril matrices, an experiment was devised as follows. Circular-cylindrical, glass tubes were fabricated having a uniform length of 87 mm and various inner diameters in the range of 2–12 mm. Stock lathyritic collagen was loaded through special silicone rubber stoppers similar to the method of Example 1.

A special holder was constructed which held the tubes between 2 acrylic end-plates. Each set of tubes, consisting of 6 glass tubes (2, 4, 6, 8, 10 and 12 mm) and one 6 mm quartz tube control, was pre-loaded and assembled in the cold room and stored in an ice bath for transport. Subsequently, each sample set was transferred to a 30° C. water bath and thermal gelation allowed to progress.

Analyses as described in Example 1 were performed on the resulting gels and dried ribbon structures. Table III compares the mechanical and optical properties of gels processed vertically and horizontally. In the tensile test, horizontally gelled samples tended to break perpendicularly across the ribbon, probably because the fibrils tend to be oriented either randomly or across the ribbon. Vertically gelled samples consistently broke in a sawtooth pattern elongated in the axial direction, supporting the conclusion that axial orientation of collagen fibrils is enhanced in this sample position.

As shown in Table III, the differences in mechanical and optical properties between vertically and horizontally gelled samples is maximized in approximately 8 mm ID tubes. In 12 mm diameter samples, mechanical strength was essentially equivalent in vertical and horizontal gels. However, optical measurements of the 12 mm samples indicated that: (1) the vertically formed gel contained an intermediate level of axially aligned fibers, while (2) the horizontally formed gel contained more randomly oriented structures. Indeed, in certain regions within the horizontal sample, collagen fibrils were found to be oriented predominantly perpendicular to the axis of the tube. Larger tubes are expected to give even more random orientation, similar to cast films, leaving these randomly oriented materials unsuitable for bioapplications.

TABLE III
EFFECT OF TUBE DIAMETER ON COLLAGEN MATRICES

| Tube/Gel Dia. (mm) | Tensile Stress* (g/mm²) | | Improvement in strength in Vertical over Horizontal (%) | Polarized Light Ratio | | Improvement in PLR in Vertical over Horizontal (%) |
| --- | --- | --- | --- | --- | --- | --- |
| | Vert. | Horiz. | | Vert. | Horiz. | |
| 2 | 1630 | 1260 | 29 | 1.7 | 1.1 | 55 |
| 4 | 980 | 830 | 18 | 4.3 | 3.6 | 19 |
| 6 | 1260 | 740 | 70 | 9.1 | 1.6 | 470 |
| 8 | 1420 | 680 | 109 | 11.7 | 0.9 | 1200 |
| 10 | 1100 | 720 | 53 | 26.2 | 8.3 | 216 |
| 12 | 830 | 820 | 1 | 8.7 | 3.4 | 156 |

*Tensile stress normalized by using a common shrinkage factor based on the typical shrinkage of 6 mm gels.

Example 4-Extrusion Orientation

Several experiments were run to demonstrate the orienting effect of laminar flow induced during extrusion. Typically, collagen monomer solution was loaded into a glass syringe mounted on a variable speed pump. An in-line filter and an extrusion tube were in liquid communication with the syringe. Various hydrophobic tube materials (e.g., polypropylene, TFE and silicone) in a variety of diameters were utilized. The apparatus was located in a 4° C. cold room, but the extrusion tube was maintained in a heated bath to cause the thermal polymerization of the monomer as it flowed through the tube. Dwell times in the tube were adjusted (depending, among other things, on tube length and bath temperature) so that the fibrillogenesis took place in approximately the time required for the solution to traverse the tube.

Several trials were run in the above described apparatus using various tubes and bath temperatures. A 3.0 mg/ml Vitrogen 100 ® monomer solution was used. A minimum residence or dwell time appeared to be necessary for coherent gels to form. Once the threshold was exceeded, the dwell time did not seem to affect the gel properties. This minimum gel time generally varied directly with tube diameter, approximately as the linear function $$t_g = d_t + 0.86,$$

where $t_g$ is the minimum gel time in minutes and $d_t$ is the tube diameter in millimeters.

Gels were cross-linked in a 1% glutaraldehyde solution for 16 hours and rinsed in distilled water for an additional 24 hours. Samples were cut and saved for property measurement.

Extrusion rate appeared to have a large effect on the gel properties. Table IV shows the effect on strength and orientation from four samples extruded through a 3.4 mm (I.D.) silicone rubber tube using 37° C. bath.

TABLE IV
EFFECT OF EXTRUSION RATE (LINEAR VELOCITY) ON COLLAGEN PHYSICAL PROPERTIES

| Sample No. | Linear Velocity (cm/min.) | Strength* (grams per denier × 10³) | Polarized Light Ratio |
| --- | --- | --- | --- |
| 411 | static gelation | 360–362 | 5.3 |
| 410 | 1.73 | 178–370 | 3.8 |
| 409 | 3.43 | 232–393 | 3.4 |
| 393 | 6.67 | 104–316 | 3.2 |

*Denier is an equivalence rating for woven materials and equals the weight (in grams) of a fiber 9000 meters long.

It is seen that increasing velocity seems to have a disruptive effect on fibril orientation. This was also true in trials using larger and smaller tubes. Coherent gels could be repeatedly produced up to at least about 6 cm/min, but a range of 1–3 cm/min is preferred.

In tubes larger than 5 mm and having lengths less than 10 times their diameter, gravity drainage of the monomer solution became a problem. It was necessary in tubing this size and larger to use tubing longer than 10 times the diameter and to begin gellation with a plug in the tube. Following the initial static gellation, the plug was removed and the pump started to extrude normally. Tubes of at least about 9.5 mm were used in this manner. Larger tubes, however, resulted in gels of poorer quality. For these reasons, tubes having diameters on the order of 6-8 mm appear to be the maximum useful sizes.

To demonstrate the effect on properties of pre-gelling the collagen solution, a trial was run wherein the syringe temperature was gradually raised from the 4° C. cold room temperature to 33° C. A 4.8 mm tube was used, along with a 37° C. bath. Samples were taken every three minutes. Both the polarized light ratio and the mechanical strength of the samples decreased dramatically in a linear fashion over the 40 minute test. We view this a further evidence that the laminar flow in the monomeric solution is the cause of orientation of the fibrils.

While the examples and text have primarily detailed the presently preferred method of practicing the invention with small tubes and convective flow it will be clear that the critical discovery of the present invention is the orientation of collagen monomer in a laminar flow field, and the subsequent gelation of the solution to maintain orientation. Therefore, other known methods of inducing flow in the collagen solution during thermal gelation are intended to be included herein.

We claim:

1. A method for producing a biomaterial implant having oriented collagen fibrils therein comprising
   (a) providing a collagen solution comprising substantially monomeric collagen,
   (b) inducing a substantially laminar flow in the collagen solution thereby orienting the monomeric collagen molecules in the flow direction,
   (c) thermally gelling the collagen solution into a collagen gel while the molecules are oriented in the flow direction,
   (d) stabilizing the collagen gel by crosslinking,
   (e) drying the stabilized collagen gel to below the point of irreversible shrinkage,
   (f) rehydrating the dried collagen gel, and
   (g) forming a biomaterial implant from the rehydrated collagen gel.

2. The method for producing a biomaterial implant as in claim 1 wherein the flow is induced in the collagen solution by the steps of introducing the collagen solution into a cylindrical tube having a cross sectional area of less than about 120 square millimeters, and heating the outer surface of the cylindrical tube at a rate which results in convective flow within the collagen solution.

3. The method of claim 2 wherein the cylindrical tube has a width of less than about two times the thickness and a height of greater than about four times the thickness.

4. The method of claim 2 wherein the tube is circular in cross section and has an internal diameter no greater than about 12 mm.

5. The method of claim 4 wherein the fibrillogenesis is induced by contacting the outer surface of the tube with a fluid having a temperature of between about 20° C. and 40° C.

6. The method of claim 5 wherein the longitudinal axis of the tube is maintained in a substantially vertical orientation during fibrillogenesis.

7. The method for producing a biomaterial implant as in claim 1 wherein flow is induced in the collagen by extruding the collagen solution through a small-diameter, elongated tube.

8. The method of claim 7 wherein the length of the tube and the flow velocity of the collagen solution are such that the solution is gelled in approximately the time required for the solution to traverse the tube.

9. The method of claim 8 wherein the flow rate of the collagen solution is less than about 6 cm/min.

10. A method for continuously producing collagen-based material having oriented collagen fibrils therein comprising
 (a) continuously forcing a solution of predominantly monomeric collagen at a flow rate of less than about 6 cm/min through an elongated tube,
 (b) heating the outer surface of the tube at a rate which causes thermal gellation in the tube,
 (c) continuously removing gelled collagen from the tube, and
 (d) stabilizing the collagen gel by cross-linking.

11. A method for producing collagen-based material having oriented collagen fibrils therein comprising
 (a) introducing a solution of predominantly monomeric collagen into a cylindrical tube having a width of less than about two times the thickness, a height of greater than about four times the thickness, and a cross-sectional area of less than about 120 square millimeters,
 (b) heating the outer surface of the cylindrical tube and, at a rate which results in convective flow within the collagen solution and a temperature therein which induces fibrillogenesis of the monomeric collagen to a collagen gel, and
 (c) stabilizing the collagen gel by chemical cross-linking, and
 (d) removing the stabilized collagen gel from the tube.

12. The method of claim 11 wherein the cylindrical tube cross section is substantially circular or square.

13. The method of claim 12 wherein the tube is circular in cross section and has an internal diameter no greater than about 12 mm.

14. The method of claim 11 wherein the fibrillogenesis is induced by contacting the outer surface of the tube with a fluid having a temperature of between about 20° C. and 40° C.

15. The method of claim 11 wherein the longitudinal axis of the tube is maintained in a substantially vertical orientation during fibrillogenesis.

16. The method of claim 11 wherein the collagen is present in solution at between about 0.6 and 3.0 mg/ml.

* * * * *